(12) United States Patent
Nagaoka et al.

(10) Patent No.: US 7,662,340 B2
(45) Date of Patent: Feb. 16, 2010

(54) EXTRACTOR CHEMICAL ANALYZER AND CHEMICAL ANALYZING METHOD

(75) Inventors: Yoshihiro Nagaoka, Tsuchiura (JP);
Naruo Watanabe, Tsuchiura (JP);
Teruhisa Akashi, Tsuchiura (JP); Yuji Miyahara, Hitachinaka (JP); Kei Takenaka, Tsuchiura (JP); Tomoki Ohashi, Tsuchiura (JP)

(73) Assignee: Hitachi High-Technologies Corporation, Tokyo (JP)

( * ) Notice: Subject to any disclaimer, the term of this patent is extended or adjusted under 35 U.S.C. 154(b) by 749 days.

(21) Appl. No.: 10/500,385

(22) PCT Filed: Dec. 28, 2001

(86) PCT No.: PCT/JP01/11620

§ 371 (c)(1),
(2), (4) Date: Jun. 28, 2004

(87) PCT Pub. No.: WO03/059484

PCT Pub. Date: Jul. 24, 2003

(65) Prior Publication Data

US 2005/0095172 A1    May 5, 2005

(51) Int. Cl.
*G01N 9/30* (2006.01)
(52) U.S. Cl. .............................. 422/72; 422/64; 436/45
(58) Field of Classification Search ............... 422/50, 422/64, 72, 99, 102; 436/45
See application file for complete search history.

(56) References Cited

U.S. PATENT DOCUMENTS

| | | | |
|---|---|---|---|
| 4,463,097 A | 7/1984 | Guigan | |
| 4,469,793 A | 9/1984 | Guigan | |
| 5,472,603 A * | 12/1995 | Schembri | ............. 210/380.1 |
| 6,063,589 A | 5/2000 | Kellogg et al. | |
| 6,706,519 B1 * | 3/2004 | Kellogg et al. | ............ 435/287.2 |
| 2002/0047003 A1 * | 4/2002 | Bedingham et al. | ......... 219/388 |

FOREIGN PATENT DOCUMENTS

| | | |
|---|---|---|
| WO | WO 95/01359 | 1/1995 |
| WO | WO 00/78455 A1 | 6/2000 |

\* cited by examiner

*Primary Examiner*—Jill Warden
*Assistant Examiner*—Natalia Levkovich
(74) *Attorney, Agent, or Firm*—Antonelli, Terry, Stout & Kraus, LLP.

(57) ABSTRACT

The invention is achieved by feeding a reagent using centrifugal force, without providing a valve for controlling the flow rate of the reagent in the reagent flow path.

A chemical analyzer is used which comprises a structure that is supported so as to be rotatable, said structure comprising a capturing section for capturing specific chemical substances from a specimen, specimen containers and reagent containers including washing solution containers.

The washing solution containers and the other reagent containers comprise a liquid outlet port which is provided at the side opposite to the rotation center side, and the capturing section is held in the structure, closer to the outer periphery side than the specimen container and washing solution and the other reagent containers, and a flow path is provided, with a bent flow path portion which returns to the rotation center side, and which at a particular stage prevents the flow of liquid from the washing solution containers to the capturing section, and at another stage, forms the liquid flow due to the centrifugal force from the rotation of the structure.

7 Claims, 14 Drawing Sheets

DIRECTION OF CENTRIFUGAL FORCE →

DIRECTION OF CENTRIFUGAL FORCE →

DIRECTION OF CENTRIFUGAL FORCE →

DIRECTION OF CENTRIFUGAL FORCE →

DIRECTION OF CENTRIFUGAL FORCE →

DIRECTION OF CENTRIFUGAL FORCE →

DIRECTION OF CENTRIFUGAL FORCE →

EXTRACTOR CHEMICAL ANALYZER AND CHEMICAL ANALYZING METHOD

TECHNOLOGICAL FIELD

The present invention relates to an extractor for extracting specific components of a liquid specimen, and to a chemical analyzer and a chemical analysis method for analyzing the extracted components.

BACKGROUND TECHNOLOGY

A purifying separation method for nucleic acid mixtures using chromatography is described in Japanese Application Patent Laid-Open Announcement No. Hei 08-501321 publication, as an extractor for extracting specific chemical substances such as nucleic acid from a specimen that includes a number of chemical substances. In this method, a nucleic acid mixture is adsorbed on an inorganic substrate such as silica gel, from an aqueous solution with high salt concentration, washed with a washing solution, and then nucleic acid is eluted with a liquid with low salt concentration. The silica gel is fixed inside a hollow cylindrical column and the solution of the nucleic acid mixture which is to be subjected to separation is introduced into the column, and the solution is passed through an inorganic substrate by vacuuming or by centrifugal separation.

In addition, WO 00/78455 publication describes a micro structure and method for examination using amplification. In this device, the purifying separation method for the nucleic acid mixture disclosed in Japanese Application Patent Laid-Open Announcement No. Hei 08-501321 was used, and the DNA mixture was passed through a glass filter as the organic base, and then passed through a washing solution and an eluent and the DNA alone was recovered. The glass filter is provided in rotatable structure, and reagents such as the washing solution and the eluent are respectively held in reagent reservoirs within the same structure. Each of the reagents is caused to flow by the centrifugal force generated by the rotation of the structure, and the reagent is passed through the glass filter by opening the valve provided in the micro flow path connecting each of the reagent reservoirs and the glass filters.

DISCLOSURE OF THE INVENTION

In the structure of WO 00/78455 publication which is the second prior art, when the valve provided in the micro flow path which connects the reagent reservoirs and the glass filters is opened, the reagent is caused to flow due to the action of the centrifugal force, and thus the reagent passes through the glass filter. Wax or the like which melts when heat is applied to the valve is used, but the reagent which is passed through may remain in the valve and contaminate the DNA which was collected from the valve portion. That is say, some DNA mixture or washing solution may remain in the valve, and in the step in which the eluent is passed through the glass filter due the centrifugal force, the DNA mixture or washing solution that remains in the valve portion may flow through.

In addition, in the method of purifying separation described in Japanese Application Patent Laid-Open Announcement No. Hei 08-501321 publication which is the first prior art, the nucleic acid mixture is introduced into a cylindrical hollow column in which silica gel is fixed, and after passing the nucleic acid mixture through the silica gel using the centrifugal force, nucleic acid only is recovered by passing the mixture through a plurality of reagents. However, neither a method for introducing the reagents into the hollow column nor a method for recovering the washing solution and the eluent which were passed through the silica gel was disclosed.

The object of this invention is to solve the above-described problems, and thus provide an extractor which can extract specific components from a liquid specimen at high purity, as well as a chemical analyzer and method for analyzing the components that were extracted.

The above-described problem can be solved by providing a reagent control section that comprises a reagent outlet port for feeding the reagent to the capturing member, and is for controlling the flow of the reagent from the reagent outlet port to the upstream side. For example, the reagent control portion may be formed so as to have a bent flow path portion in which the flow path which is connected to the container outlet section bends back closer to the rotation center side than the position of said outlet portion. In addition, in this invention, the analyzer has a split configuration, and may be formed in a sector shape or in a rectangular shape, and has a rotatable structure.

Alternatively, the problem may be solved by providing a reagent outlet port for feeding the reagent to the capturing member, and providing a portion of the flow path that allows the reagent outlet port and the capturing member to communicate, such that the flow path downstream side is closer to the rotation center side than the flow path upstream side.

It is particularly favorable for the flow path downstream side to be provided closer to the rotation center side than the reagent outlet port.

Alternatively the problem may be solved by separately holding a number of washing solutions and eluents as the reagent, including a reagent outlet port for feeding each reagent to the capturing member, and positioning the reagent outlet port at the rotation center side to the same extent as the reagent outlet for the washing solution to be used in the subsequent washing step.

It is particularly favorable for the reagent holding section to communicate with the inside of the structure.

It is also particularly preferable for a reagent control section to be provided for controlling the flow of the reagent to the upstream side from the reagent outlet port.

It is also particularly preferable that the reagent control section is a vent hole which can be opened, as well as a hole forming mechanism.

It is also preferable that the reagent control section is a reagent dispenser.

It is also particularly preferable that light is irradiated into the reagent holding section to thereby increase the temperature.

It is also particularly preferable that a plurality of structures which are supported so as to be rotatable are disposed in the peripheral direction of other rotating structures.

It is to be noted that in the present invention also, the washing solution and the eluent are generally referred to as reagent, but where it is necessary to specify, they are specifically referred to as washing solution, eluent or mixture and the like.

PREFERRED EMBODIMENTS OF THE INVENTION

An example of the gene analyzer using the extractor of this invention is described in the following, with reference to FIGS. 1-11.

Figure 1:
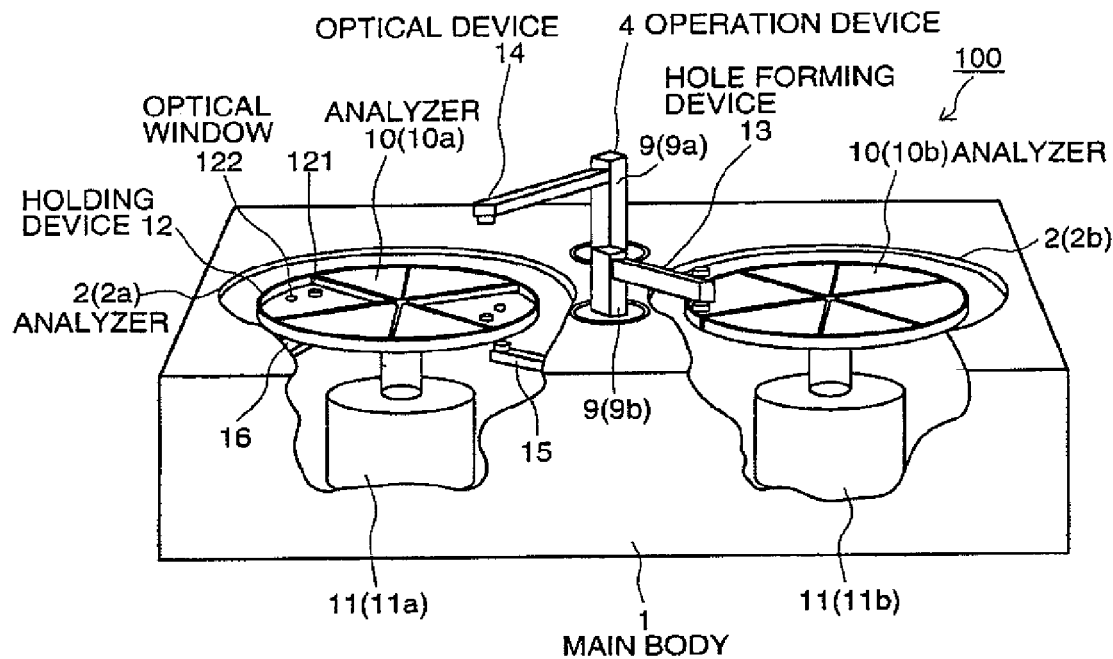
FIG. 1 shows an overall structural view of the chemical analyzer according to the present invention.
Figure 2:
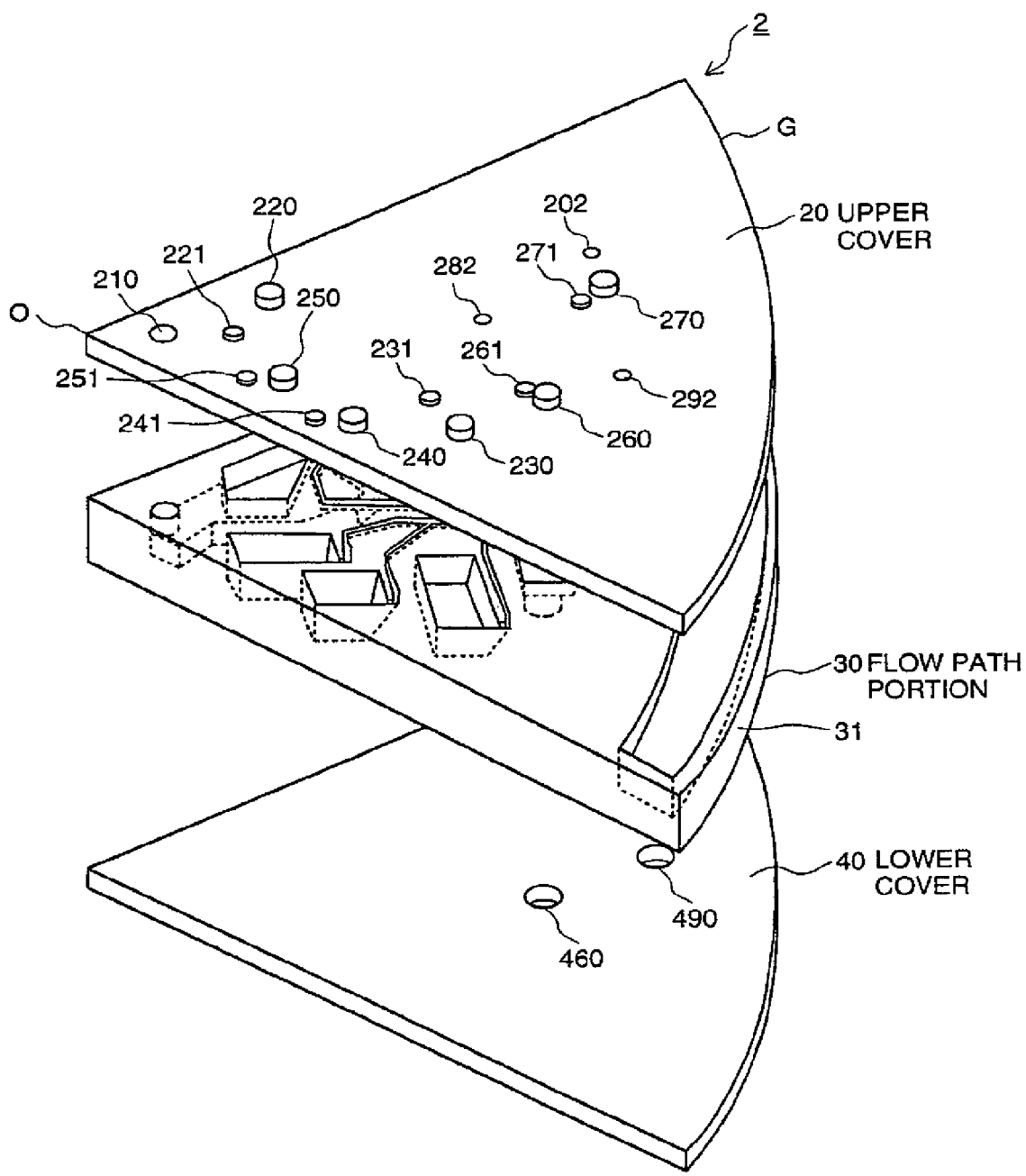
FIG. 2 is a structural view of the analyzer according to an embodiment of the present invention.

FIG. 1 is an overall structural view of a gene analyzer according to the present invention. The chemical (gene) analyzer 100 comprises: main body 1; analysis disk 2; operations device 4 which comprises a measuring device and an operations machine; and a control and recording device (not shown) which controls the entire device and the records the measurement results. FIG. 2 shows 2 analysis disks (2a and 2b), but the device may have only 1 analysis disk.

The analysis disk 2 comprises a holding disk 12 which is supported so as to be rotatable by motor 11 (11a and 11b) and a plurality of sector-shaped analyzers 10 which are positioned by projections 121 which are on top of the holding disk 12.

There are 6 analyzers 10 mounted in each holding disk 12 and each one forms an angle of approximately 60° towards the sector center (rotation center) and in total they form approximately 360°. The outer periphery of the holding device 12 has a wall in the upper direction that has tray shape when the overall structure is viewed. Penetrating optical windows 122 are formed so as to align with the projections 121.

The sector-shaped disk configuration includes a semi-circular disk configuration. This device comprises a structure such as a disk which is supported so as to be rotatable, and if the structure is formed as described in the following, and a capturing section is provided for capturing specific chemical substances from the specimen, an extractor is formed.

The operation device 4 comprises a support column 9, and an upper optical device 14 which is held on the upper side of 9 (9a), and a separate operations device (not shown) comprises a lower optical device 15, and light penetrates the optical device 15 in accordance with the position of each optical window 122. As described hereinafter, the upper optical device 14 and the lower optical device 15 are used for increasing the temperature of the liquid and for detecting desired substances (specific chemical substances) in the liquid. The support 9 (9b) has a hole forming device 13 that can form a hole in each of the analyzers 10. As a result, as described hereinafter, the flow of the liquid can be controlled, and the control section is thereby formed.

In addition, there is a position detector at the lower part of the holding disk 12. FIG. 2 is a structural view of the analysis disk 2. The analysis disk 2 comprises an upper cover 20, a flow path section 30, and a lower cover 40 which are all joined together. The flow path section 30 comprises a wall 31 which was described heretofore.

From the sector center O to the outer periphery G, the upper cover 20 has provided thereon, a specimen inlet port 210, and reagent inlet ports 220, 230, 240, 250, 260, 270, and vent holes 202, 221, 231, 241, 251, 261, 271, 282, and 292 which contact the reagent inlets. Thus each of the reagents can be loaded into the device.

The lower cover 40 includes a positioning hole 460 and a flow path section optical window 490. The analysis disk 2 is positioned by the positioning hole 460 and the projection 121 of the holding disk 12 being engaged.

Figure 3:
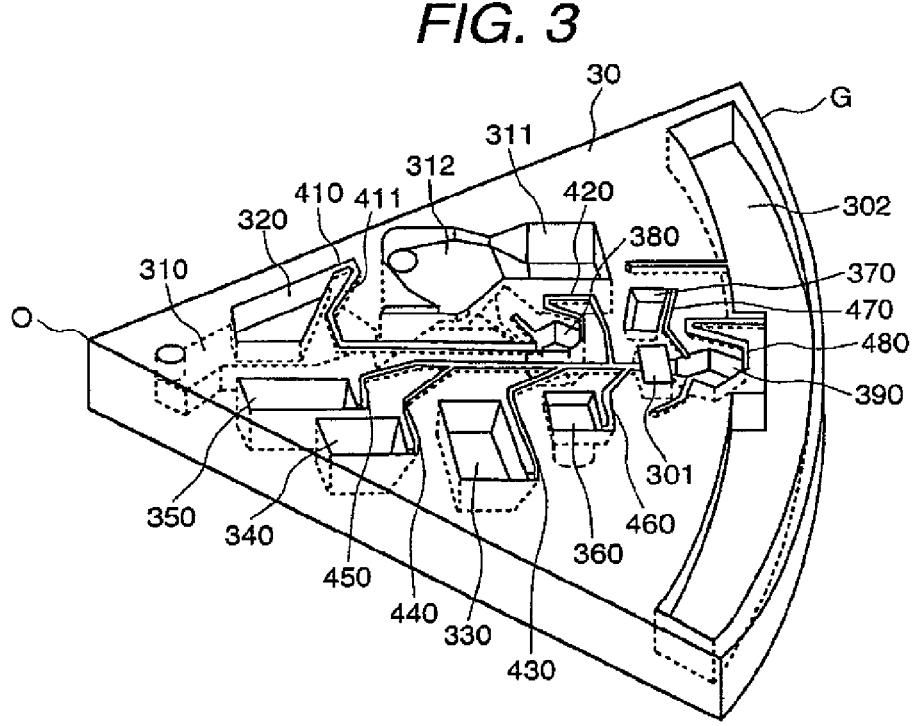
FIG. 3 is a structural view of a flow path portion according to an embodiment of the present invention.

The structure of flow path portion 30 is shown in FIG. 3. The example of the flow path portion 30 that is shown in FIG. 3 shows the extractor that separates serum from whole blood, and then extracts the nucleic acid from the virus in the serum, as well as the chemical analyzer that carries out analysis.

The following is a description of the operations of extraction and analysis of the virus nucleic acid using whole blood as the specimen.

The flow path portion 30 has a specimen container 310, 1 (in the strict sense) reagent container 320, serum holding section 312, and serum separating section 311 which are arranged on one side (the upper side in the drawing) from the sector-shaped center O (also referred to as the main side) to the outer periphery G so as to be partially or completely embedded. The specimen container 310, a third washing solution container 350, a second washing solution container 340, and a first washing solution container 330 are arranged at the other side. The first reagent container 320, the serum holding section 312, the serum separating section 311, the first washing solution container 330, the second washing solution container 340, the third washing solution container 350 and the mixture container 380 described hereinafter, are all generally referred to as the reagent container. Due to this arrangement, firstly, the separated chemical substance storage container is arranged at the inside of the outer frame container, from the sector main portion which is toward the outer periphery side, and for example, the serum storage container (serum holding section 312) is positioned at one side of the flow path section 30 which is the outer frame container. The serum separating section 311 is adjacent to the serum holding section 312. Some of the reagent containers other than the serum storage container are arranged at the other side, and the rest are arranged on either the one side or on the other side. An analysis section which is described hereinafter is arranged on the outer periphery side of these containers, and each of the containers has an inlet section at the main side of the sector and an outlet section at the outer periphery side. Also the discharge fluid storage containers 302 are provided at the outer periphery side along the outer periphery curved portion or along the straight portions of the analysis section. In addition, an appropriate flow path that connects the containers is provided, and this flow part has a bent portion which is described hereinafter.

In the analysis section, the eluent container 360 and the mixture container 380 are provided at the upstream side of the nucleic acid capturing section 301, while the eluent recovery container 390 is provided at the downstream side thereof. An amplifying solution storage container 370 is upstream of the eluent recovery container 390 and a discharge solution storage section 302 is downstream thereof and provided along most of the outer periphery G.

The reagent container 320 and the mixture container 380 are connected by the narrow flow path 410; mixture container 380 and nucleic acid capturing section 301 are connected by the narrow flow path 420; and the first washing solution container 330, the second washing solution container 340, the third washing solution container 350, and the eluent container 360 are connected to the nucleic acid capturing section 301 by the narrow flow paths 430, 440, 450 and 460 respectively. The nucleic acid capturing section 301 has a nucleic acid capturing member in the inside thereof, and the aforementioned capturing section is formed. The capturing section has an eluent recovery container (liquid recovery container) 390 connected thereto. The eluent recovery container 390 and the amplifying solution storage container 370 are connected by the narrow flow path 470, while the eluent recovery container 390 and the discharge fluid storage container 302 are connected by the narrow flow path 480.

The liquid outlet ports 303 for the containers 320, 330, 340, 350, 360, 380, 370, and 390, are formed so as to jut from the outer periphery G side, and this jutting portion is provided at the side opposite to the rotation center side.

Each of the flow paths 410, 420, 430, 440, 450, 460, 470, and 480 has a portion which is returned by being bent back closer to the rotation center side than to the liquid outlet port. In FIG. 3, all of the portions which have been returned by being bent have not been numbered since this may make the drawing unclear, and thus only 411 has been numbered for the flow path 410. The other numbers are shown in FIG. 6.

Figure 4:
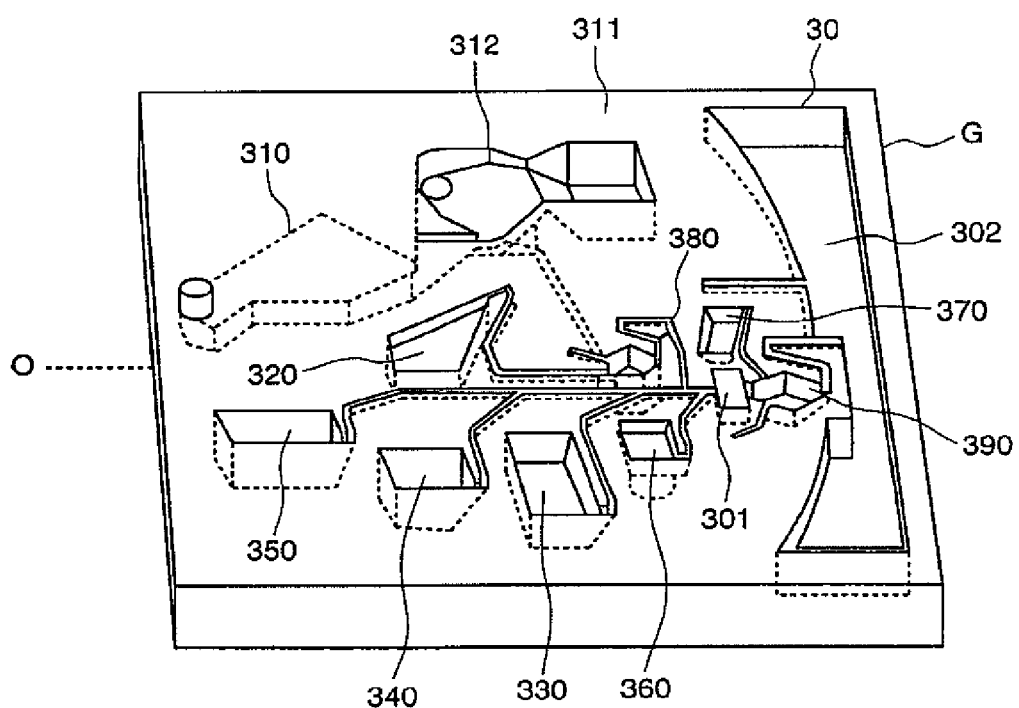
FIG. 4 is a structural view of another example of the embodiment shown in FIG. 3.

FIG. 4 shows a modified example of the analysis disk shown in FIG. 3, which has a rectangular shape, and is disposed symmetrically on the holding disk 12 such that rotation center O is its center. The configuration is the same as that described in FIG. 3 and thus the description will not be repeated.

FIG. 5 shows the vertical arrangement relationship between the specimen container 310, the serum separating section 311, the serum holding section 312, and the serum storage container 313. Directly beneath the serum holding section 312 is the serum storage container 313. Also, FIG. 6 shows a cross-section of the vertical arrangement relationship between these containers and each of the vent holes. The specimen container 310 is provided under the reagent container 321, and extends in the direction of the serum separating section 311 and serum holding section 312.

The separating agent 314 is provided vertically along almost the entire length of the overall width of the serum separating section 311.

When the analysis disk 2 is rotated by the motor 11, the centrifugal force operates from the rotation center side toward the outer periphery G as shown by the arrows in FIG. 4 and FIG. 5.

Figure 7:
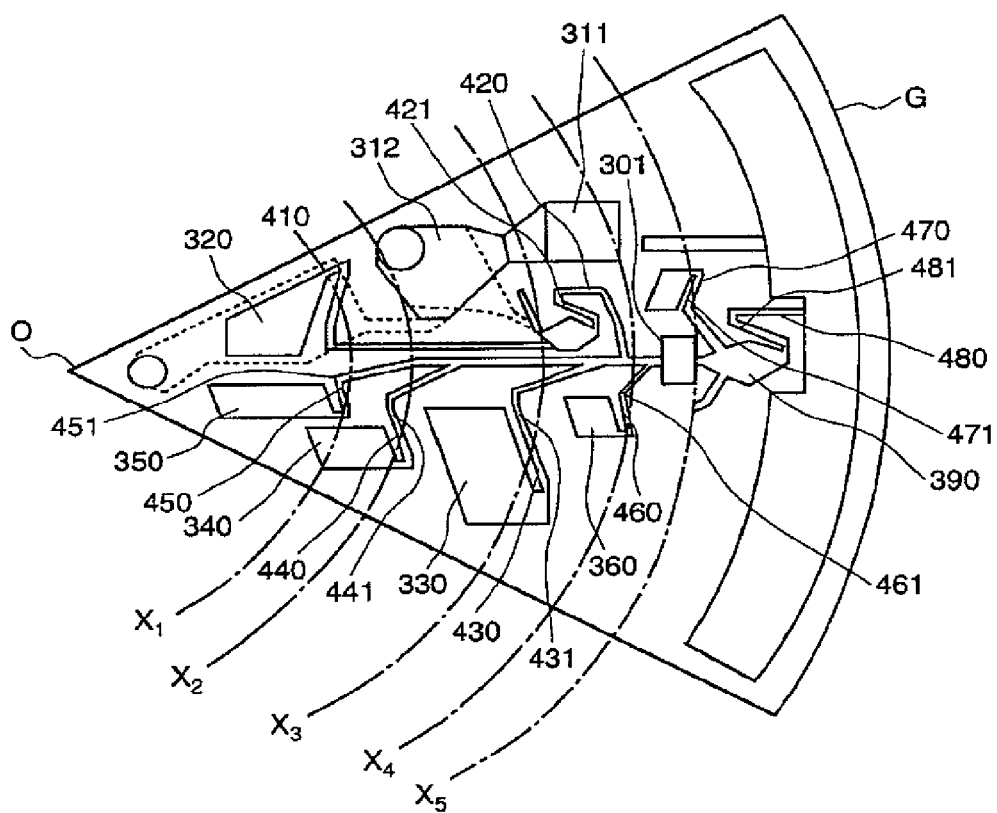
FIG. 7 is a top view of the analyzer according to an embodiment of the present invention.

FIG. 7 shows the positional relationship of the arrangement of the containers and the flow path from the rotation center side to the outer periphery G. The serum separating section 311 and the serum holding section 312 are disposed on the curve $X_3$ when viewed from the center, while the nucleic acid capturing section 301 is substantially disposed on the curve $X_5$ and thus is a position with a larger centrifugal force. In the figures, the flow paths 410, 420, 430, 440, 450, 460, 470 and 480 respectively have return portions 411, 421, 431, 441, 451, 461, 471 and 481 which are bent at the center O side.

The following is a description of the operations of extraction and analysis of the viral nucleic acid using whole blood as the reagent. The flow of the extraction and analysis operations are as shown in FIG. 10.

Figure 10A:
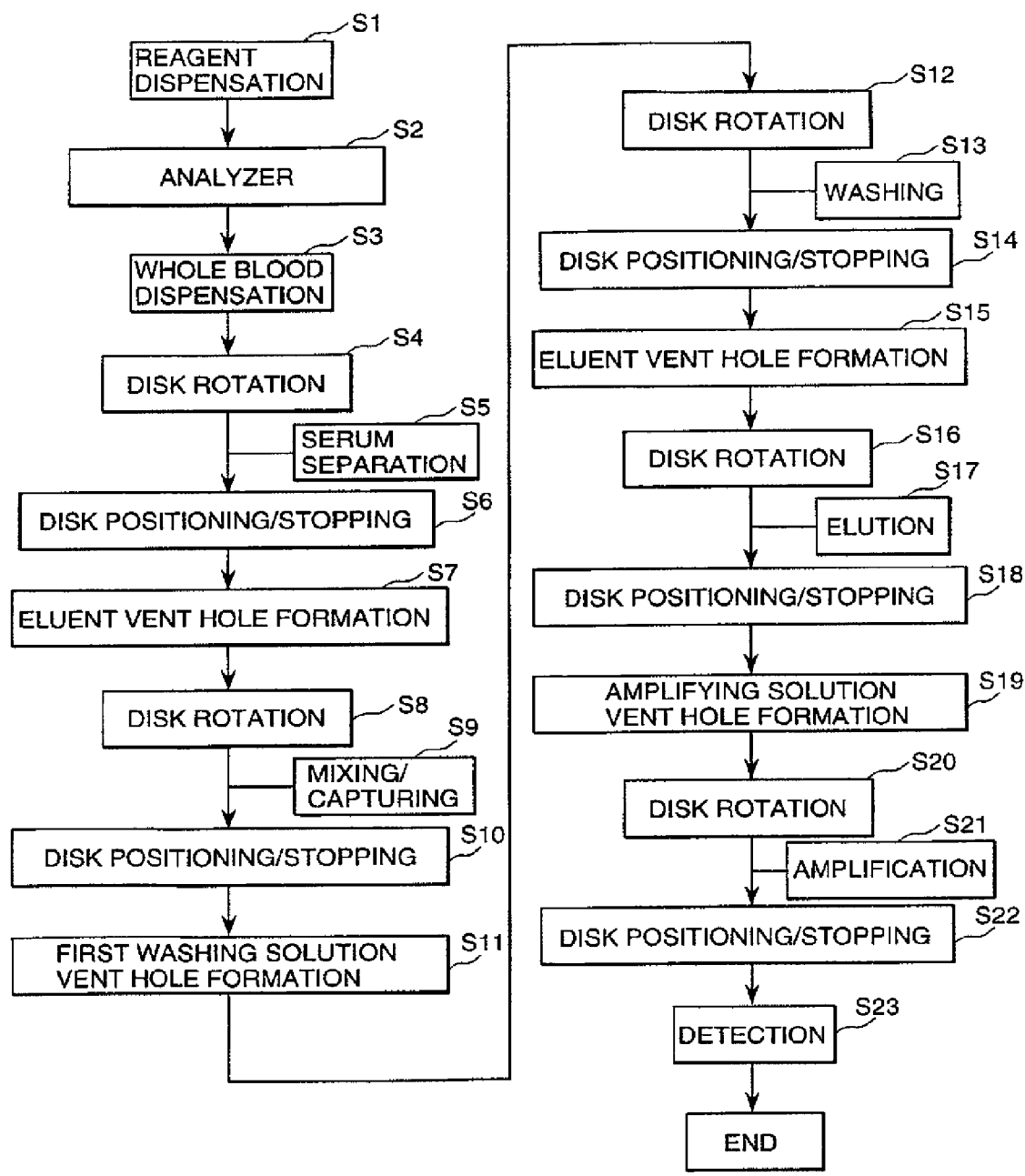
FIG. 10 is explanatory diagram showing the steps for the analysis operation according to an embodiment of the present invention.

In FIG. 10a, the operator dispenses the reagent into each of the reagent containers 320, 330, 340, 350, 360, and 370 through the reagent inlet ports 220, 230, 240, 250, 260, and 270 from the upper cover 20 of the analyzer 10 (S1), and then each of the reagent inlet ports was covered. After the reagent is introduced into the necessary number of analyzers 10 in accordance with the number of analyses, the analyzers 10 are mounted to the holding disk 12 (S2).

Next the whole blood is introduced into the reagent container using the reagent inlet port 210 (S3). After introduction of the whole blood, the holding disk 12 is rotated by the motor 11 (S4). The whole blood which was introduced into the specimen container 310 flows to the outer periphery side due to the centrifugal force generated by the rotation of the holding disk 12. The flow state of this whole blood is shown in FIG. 5. The serum storage container 313 which will be described hereinafter is positioned directly beneath the serum holding section 312, and the serum storage container 313 and the serum holding section 312 communicate with each other via the serum outlet port 315. However in FIG. 5, in order to show the flow state of the serum, the serum storage container 313 is shown separate from the serum holding section 312. The positional relationship of the whole blood flow section in the vertical direction is shown in the vertical cross section of the analysis disk (FIG. 6). It is to be noted that FIG. 6 also shows the reagent containers, the mixture section and the discharge fluid containers described hereinafter.

Figure 5A:
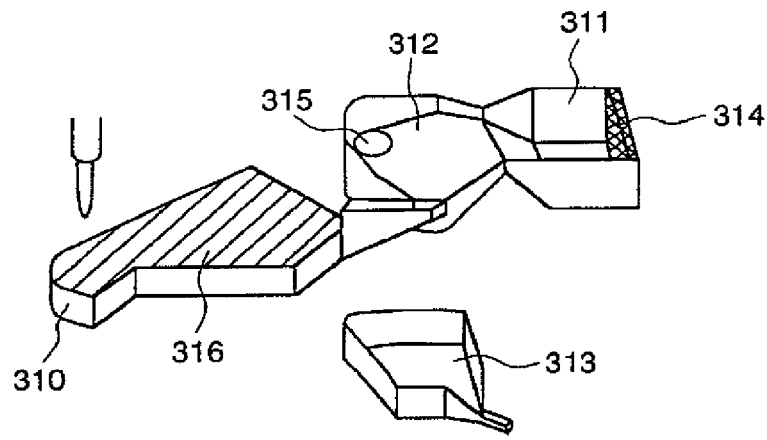
FIG. 5 is an explanatory view of the operation of the blood cell separation section according to an embodiment of the present invention.
Figure 5B:
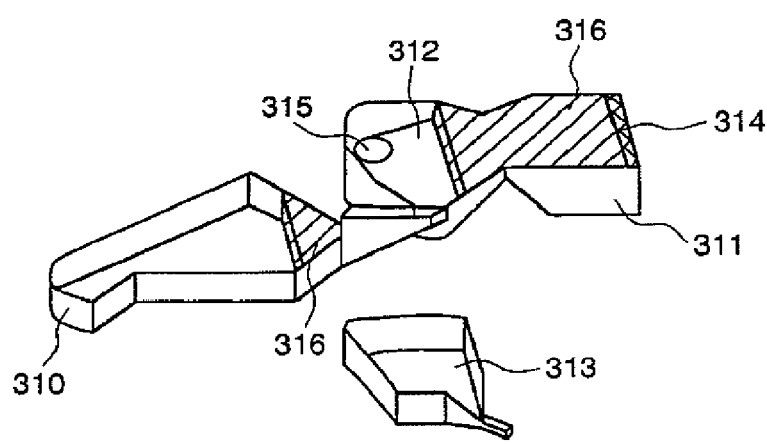
Figure 5C:
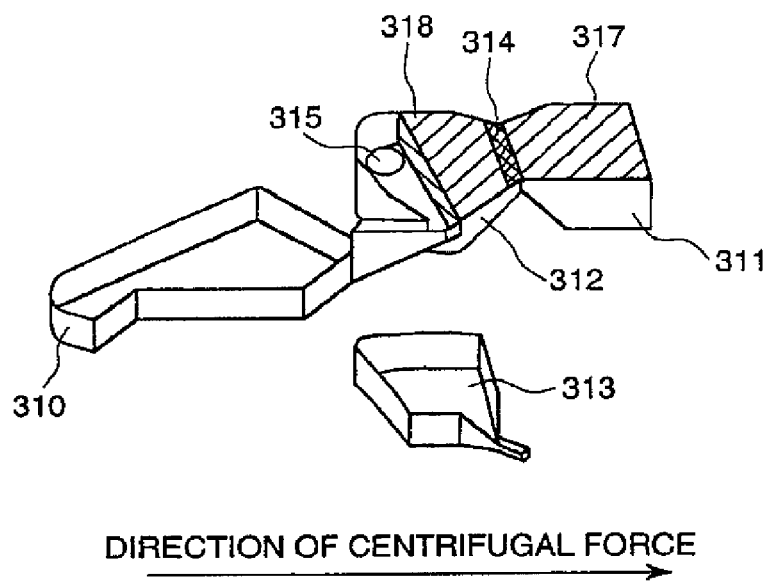
Figure 5D:
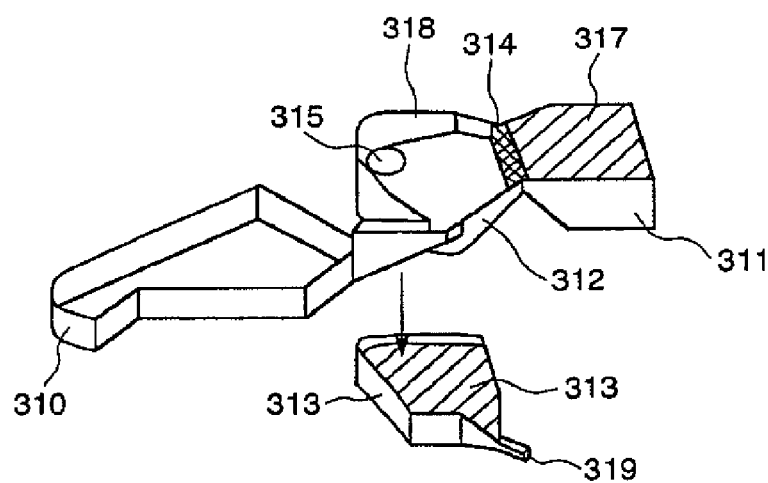
Figure 6A:
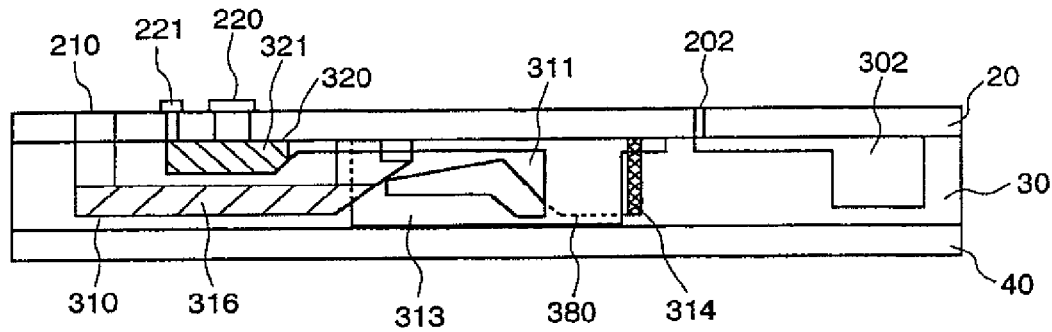
FIG. 6 is a cross-section of the analyzer according to an embodiment of the present invention.
Figure 6B:
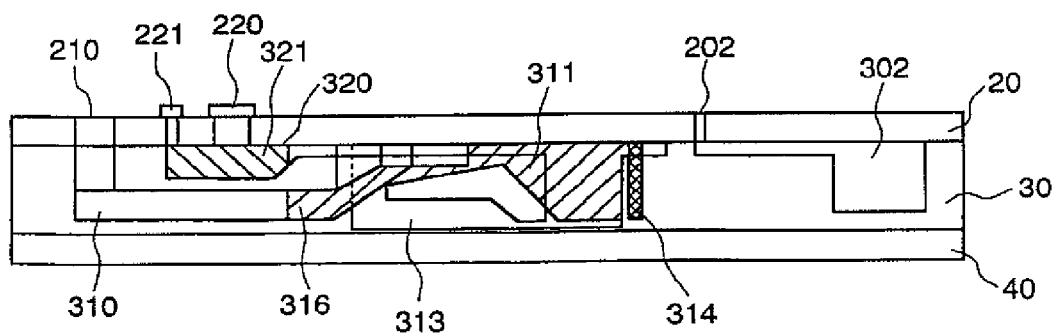

As shown in FIGS. 5(a) and 6(a) the whole blood 316 which was introduced is held in the specimen container 310. When the holding disk 12 is rotated (FIG. 5(b) and FIG. 6(b)), the whole blood 316 is caused to flow to the blood cell separating section 311 due the centrifugal force. The separating agent 314 is introduced into the serum separating section 311 beforehand. The specific gravity of the separating agent 314 is larger than that of the serum and less than that of the blood cells. When the rotation speed of the holding disk 12 is increased to thereby cause gradual separation of the blood cells and the serum due to the difference in the specific gravity, the separation agent 314 is positioned between the blood cells 317 and the serum 318, and thus the blood cells 17 and the serum 318 are separated (S5) (FIG. 5(c) and FIG. 6(c)). When the rotation of the motor 11 is stopped (S6), only the serum flows out via the serum outlet port 315 from the serum holding section 312 to the serum storage container 313 which is directly beneath (FIG. 5(d) and FIG. 6(d)).

When this series of serum separation operations are done, the vent holes 221, 231, 241, 251, 261, and 271 of the reagent containers on the upper cover are covered, and thus in an airtight state. The reagents attempt to flow out to the outer periphery of the reagent container due to centrifugal force, but because air does not enter the container, the pressure inside the reagent container is reduced, and this counteracts the centrifugal force and thus the reagent cannot flow. However when the centrifugal force is increased by increasing the rotation speed, the pressure inside the reagent container gradually decreases, and when the pressure falls below the saturation vapor pressure, air bubbles are generated. As shown in FIG. 7, by having a bent flow path structure (the return flow path portions 410, 420, 430, 440, 450, 460, 470 and 480 in FIG. 7) in which the reagent which flows from the outer periphery side of each of the reagent containers is returned to the inner periphery side, pressure reduction in the reagent container is controlled, and air bubble generation is prevented. This bent flow path structure (bent portion) may have a curved or bent configuration. In this manner, at the time of the serum separation operation shown in FIG. 5 and FIG. 6, the reagent (reagent 321 in the case of FIG. 6) is held in the reagent container 320 and do not flow out.

When the serum separation operation is complete, the serum 318 is stored in the serum storage container 313, and the hole forming device 13 forms one hole in each vent hole cover at the upper portion of each of the reagent containers, the motor 11 rotates, and each of the reagents is caused to flow due to the centrifugal force.

The following describes the operation after completion of the serum separation.

The solution for dissolving the membrane protein of the virus in the serum is dispensed into the solution container 320. After the hole forming device 13 forms holes in the cover of the solution vent hole 221 (S7), when the motor 11 is rotated (S8) the solution is caused to flow due to action of the centrifugal force, into the mixture container 380 via the flow path 410 that has the solution return portion 411, from the reagent container 320 which is a solution container. At this time, the serum in the serum storage container 313 also flows to the mixture container 380 due to the action of the centrifugal force.

Figure 8A:
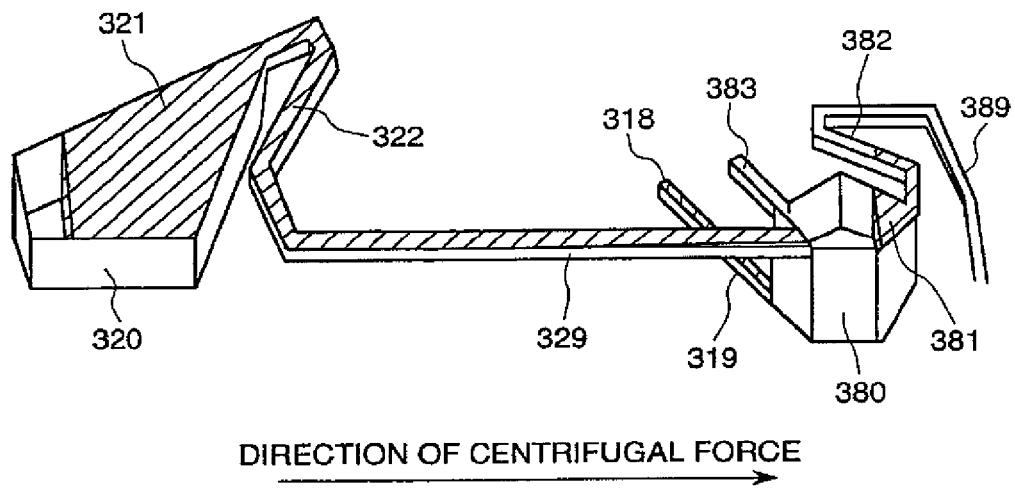
FIG. 8 is an explanatory view of the operation of the mixing section according to an embodiment of the present invention.
Figure 8B:
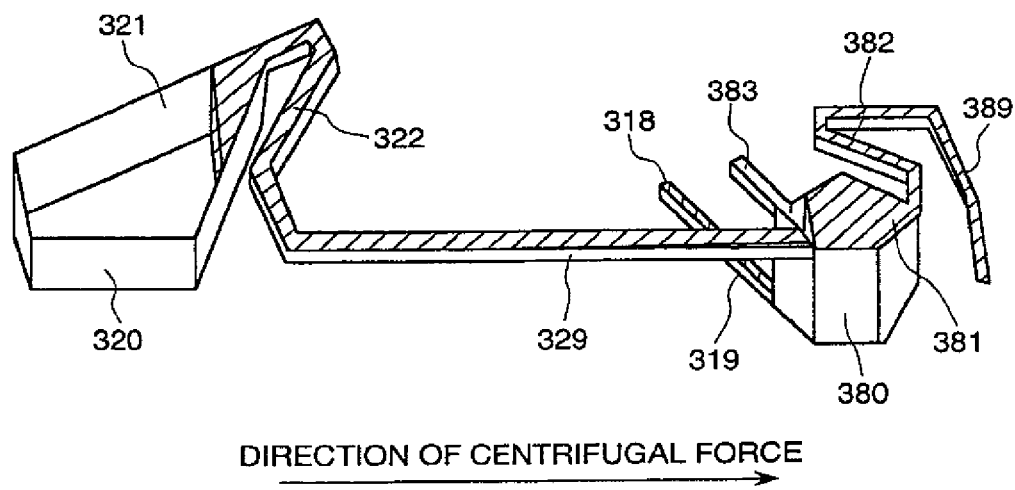

FIG. 8 shows the flow of the serum and the solution into the mixture container 380. The mixture container 380 communicates with the serum storage container 313 via the serum flow path 319, communicates with the solution storage container 320 via the solution outflow path 329, and communicates with the outside from the mixture container vent hole 282 (FIG. 2) via the mixture container vent flow path 383. The serum 318 and the solution 321 flow to the mixture container 380, and because the flow path has a structure (mixture return flow path 382) in which the serum and solution mixture 381 is returned to the inner periphery side, the solution is temporarily held in the mixture container 380 (FIG. 8(a)), and the serum and the solution are sufficiently mixed in the mixture container 380. As shown in FIG. 8(b), the volume of mixture in the mixture container 380 increases and flows out from the mixture return flow path 382 to the nucleic acid capturing section 301 (FIG. 3) via the mixture outflow path 389.

The solution dissolves the membrane of the virus or bacteria in the serum and elutes the nucleic acid, and in addition, the adsorption of nucleic acid is facilitated in the nucleic acid capturing section 301. The reagent used as this solution may be guanidine hydrochloride for elution and adsorption of DNA, or guanidine thiocyanate for RNA, and the nucleic acid capturing member may be a porous material such as quartz or glass, or a fibrous filter or the like.

In this manner, when the solution and the serum mixture passes the nucleic acid capturing member, the nucleic acid is adsorbed by the nucleic capturing member and the liquid flows to the eluent recovery container 390.

Figure 9A:
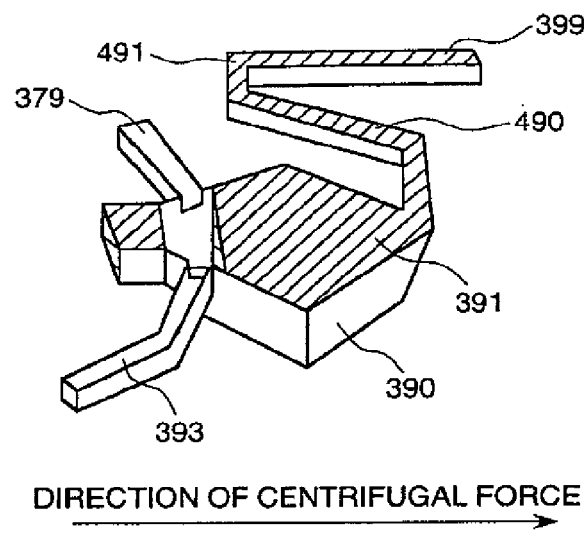
FIG. 9 is an explanatory view of the operation of the eluent recovery section according to an embodiment of the present invention.

As shown in FIG. 9, the eluent recovery container 390 communicates with amplifying solution storage container 370 (FIG. 3) via the amplifying solution outflow path 379, and also communicates with the outside, from the eluent recovery vent hole 292 (FIG. 2) via eluent recovery vent flow path 393. The discharge fluid 391 which is generated after the nucleic acid capturing section 301 is passed, is temporarily held in the eluent recovery container 390 due to the discharge return flow path 392 as is the case for the mixture container 380. However, because the volume of the eluent recovery container 390 is sufficiently smaller than the discharge fluid amount, in the end, as shown in FIG. 9(a), discharge fluid goes beyond the innermost periphery of the discharge fluid return flow path 392 and flows out to the discharge fluid storage container 302 (FIG. 3) via the discharge fluid outflow path 399.

Next the motor 11 is stopped (S10), and after a hole is formed by the hole forming device 13 into the cover of the first washing solution vent hole 231 for supplying air to the first washing solution container 330 (S11), the motor 11 is rotated again (S12), and due to the action of the centrifugal force, the first washing solution flows from the first washing solution container 330 to the nucleic acid capturing section 301 via the flow path 430 that has the first washing solution return portion 431, and the unnecessary components such as the protein and the like which adhere to the nucleic acid capturing member is washed (S13). The first washing solution may, for example, be the above described solution, or the solution with reduced salt concentration may be used.

The discharge fluid which has been washed, flows to the discharge fluid storage container 302 via the eluent recovery container 390 in the same manner as the mixture described above.

The same washing operation is repeated a number of times. For instance, in the example of FIG. 3, immediately after the washing with the first washing solution, with the motor in the stopped state (S14), a hole is formed by the hole forming device 13 into the cover of the second water solution vent hole 241 for supplying air to the second washing solution container 340 (S15), and the motor is stopped again (S16), and the unnecessary components such as the salt and the like which adhered to the nucleic acid capturing member are washed. Ethanol or ethanol and water solution may, for example, be used as the second washing so lution.

Likewise, a hole is formed into the cover of the third washing solution vent hole 251 for supplying air to the third washing solution container 350, and the unnecessary components such as the salt and the like which adhered to the nucleic acid capturing member are washed. Ethanol or ethanol and water solution may, for example, be used as the third washing solution. By causing the washing solutions to flow sequentially, starting with the first washing solution, the contaminants are reduced.

In this manner, after the nucleic acid capturing member is washed and only the nucleic acid is adsorbed, the process proceeds to the nucleic acid elution step (S17).

That is to say, when the motor is in a stopped state, a hole is formed by the hole forming device 13 in the cover of the eluent vent hole 261 for supplying air to the eluent container 360, and the motor 11 is rotated again, and the eluent is caused to flow to the nucleic acid capturing member. The eluent is a liquid for eluting the nucleic acid from the nucleic acid capturing member, and water or a water solution prepared such that the pH is 7-9 may be used. In order to facilitate elution, it is preferable that the eluent is heated to 40° C. The upper optical device 14 in FIG. 1 may be used for heating, and light may be irradiated from above the eluent container 360.

Figure 9B:
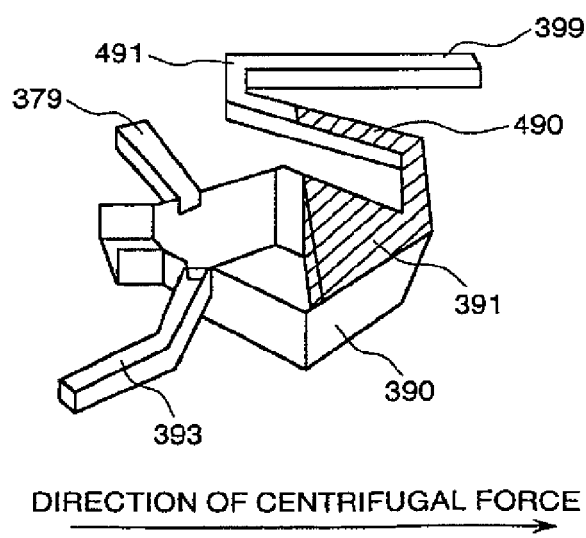

After the eluent passes the nucleic acid capturing member, it flows to the eluent recovery container 390. If the amount of eluent is sufficiently smaller than the volume of the eluent recovery container 390, as shown in FIG. 9(b), the discharge fluid cannot go beyond the innermost periphery side of the flow path 490 which has the discharge fluid return portion 491 and is held in the eluent recovery container.

Next, with the motor in a stopped state (S18), a hole is formed into the cover of the amplifying solution vent hole 271 for supplying air to the amplifying solution storage container 370 (S19), and the motor 11 is rotated once again (S20), and the amplifying solution is caused to flow into the eluent recovery container 390 (S21). The amplifying solution is a reagent for amplifying and detecting nucleic acid, and examples includes deoxynucleoside triphosphate or DNA synthetic enzyme and fluorescent reagents and the like. Depending on the amplifying method, the amplifying solution may be heated by irradiating light from above the eluent recovery container 390, using the upper optical device 14.

Next, the lower optical device 15 is moved under the eluent recovery container 390, and the amount of fluorescent emission, for example, is detected.

Figure 11:
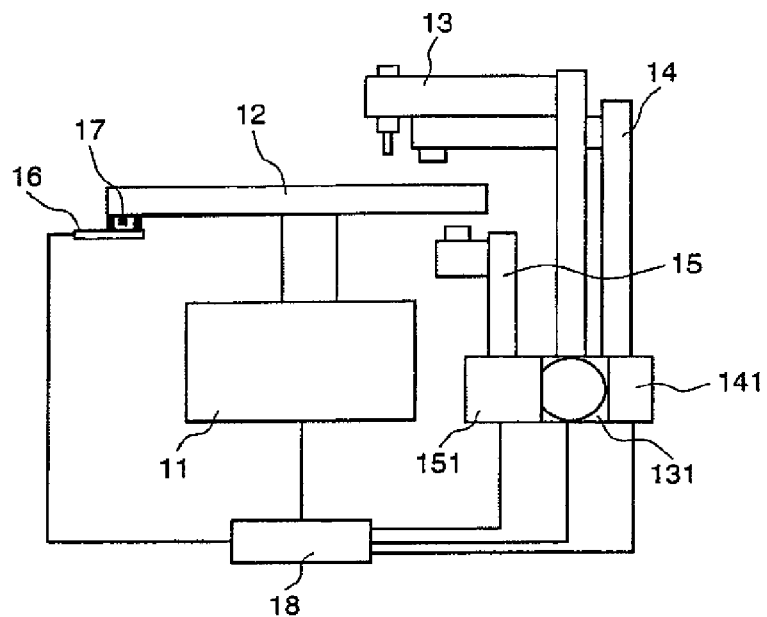
FIG. 11 is a circuit diagram of the positioning mechanism according to an embodiment of the present invention.

The hole forming device and the heater must be fixed at a predetermined position in the holding disk 12 at the time of detection. As shown in FIG. 11, the holding disk 12 has a positioning projection 17, and the rotation position of the holding disk is detected by the position detector 16. The rotation of the motor 11 and the rotation and vertical movement of the hole forming device 13, and the rotation, radiation and detection of the upper optical device 14 and the lower optical device 15 are controlled by the controller 18.

Figure 12:
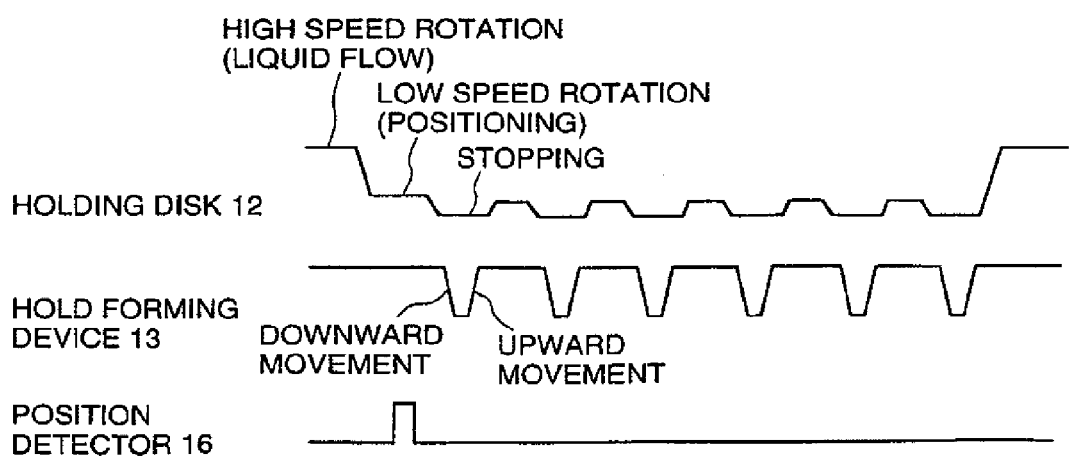
FIG. 12 is a timing chart of the positioning operation according to an embodiment of the present invention.

As an example, FIG. 12 shows the operation timing of the hole forming device 13. The holding disk 12 reduces the rotation speed after flow of the whole blood or the reagents is complete, and low speed rotation for positioning is maintained. When the position detector 16 detects the projection 17 for positioning, the holding disk 12 is stopped (S22), and after the hole forming device 13 is moved downwards and a hole is formed in the cover of each reagent storage container, the hole forming device is moved upwards again. After hole formation, the holding disk 12 rotates the reagent storage container into which the hole has been formed at a low speed such that the reagent does not flow out, to the position of the next analyzer. That is to say, in the case where 6 analysis disks are mounted, the containers are rotated by 60° and then stopped, and then the same hole-forming operation is repeated. The position where the analysis disk is mounted can be determined, for example, by irradiating light from the flow path optical window 490 using the lower optical device and checking the reflected light. After holes are formed in all of the analysis disks, the holding disk rotates at a high speed causing the reagents to flow.

According to the examples of the present invention, it is not necessary to provide a valve for controlling the flow of each reagent in the flow path as was described above, and thus liquid does not remain on the valve portion that is in the flow path. Contamination caused by the reagent from the previous step is prevented, and specific components of the liquid specimen such as nucleic acid can be extracted with high purity, and thus highly accurate analysis can be done (S23).

Figure 10B:
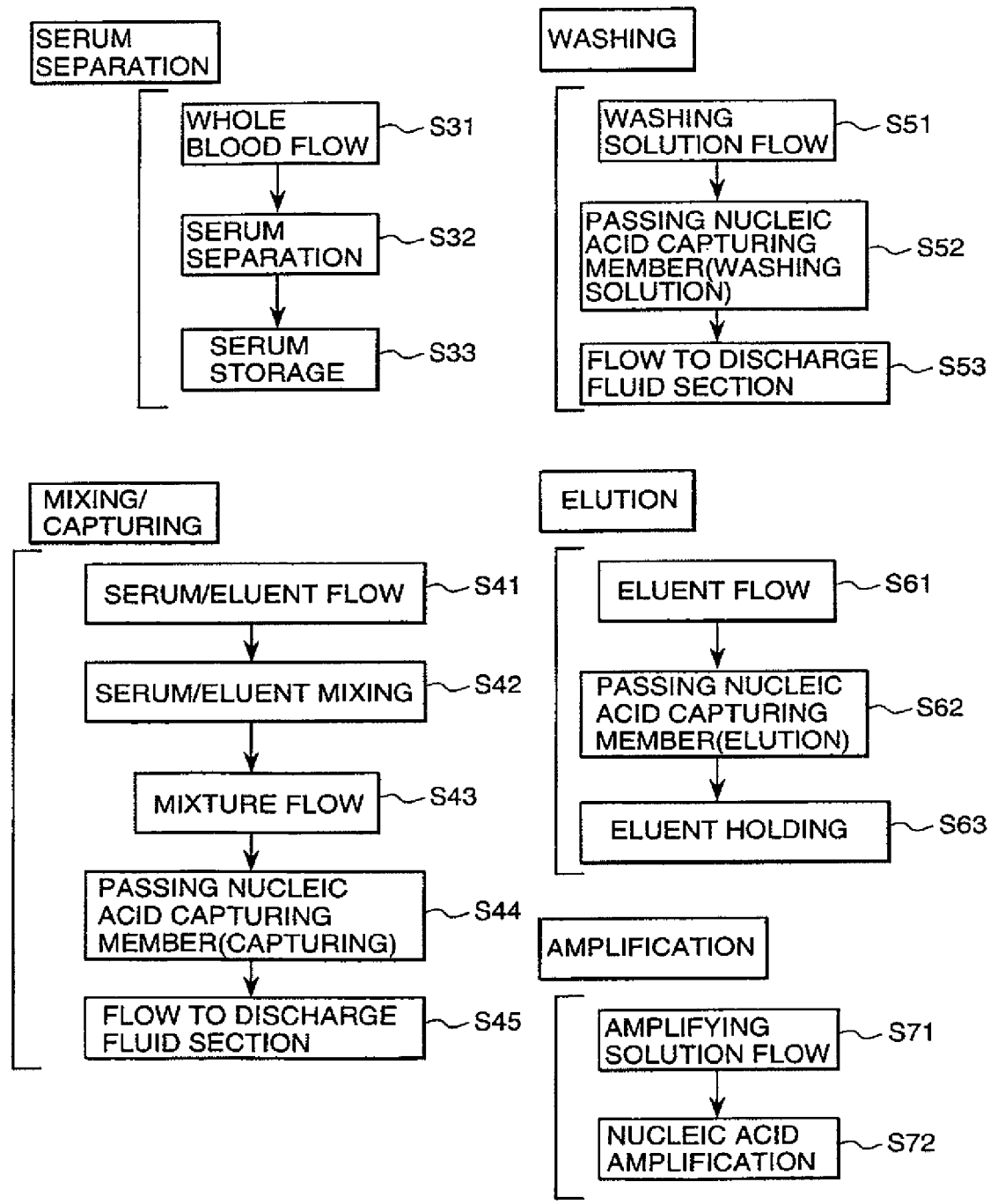

In FIG. 10(b) the serum separation is carried out by the steps of whole blood flow (S31), serum separation (S32) and serum storage (S33).

Mixing and capturing are carried out by the steps of the serum and solution flow (S41), serum and solution mixing (S42), mixture flow (S43) passing the nucleic acid capturing member (S44), and flow to discharge fluid portion (S45).

The washing is carried out by the steps of washing solution flow (S51), passing the nucleic acid capturing member (washing) (S52), a nd flow to the discharge portion (S53).

The elution is carried out by the steps of eluent flow (S61), passing the nucleic acid capturing member (elution) (S62), and eluent holding (S63).

In addition, amplification is carried out through the steps of the amplifying solution flow (S71) and the nucleic acid amplification (S72).

According to the example of the present invention, liquid is prevented from remaining in the flow path. In the case where liquid such as the washing solution remains in the flow path, when the analysis disk is being rotated in order to feed amplification solution, the washing solution flows and is mixed in the eluent recovery container 390, and thus the amplification reaction maybe impeded. In view of this, by designing the reagent flow control mechanism according to this invention, liquid is prevented from remaining in the flow path, and in addition even when some liquid remains, the liquid does not flow into the eluent recovery container. For example, if the structure is such that the reagent is returned to the inner periphery, as is the case of the first washing solution return flow path 430 shown in FIG. 7, the liquid does not flow all the way out due to centrifugal force and remains in the first washing solution storage container 330 is held in the first washing solution return flow path 430, and thus does not flow to the washing solution recovery container side.

Figure 13:
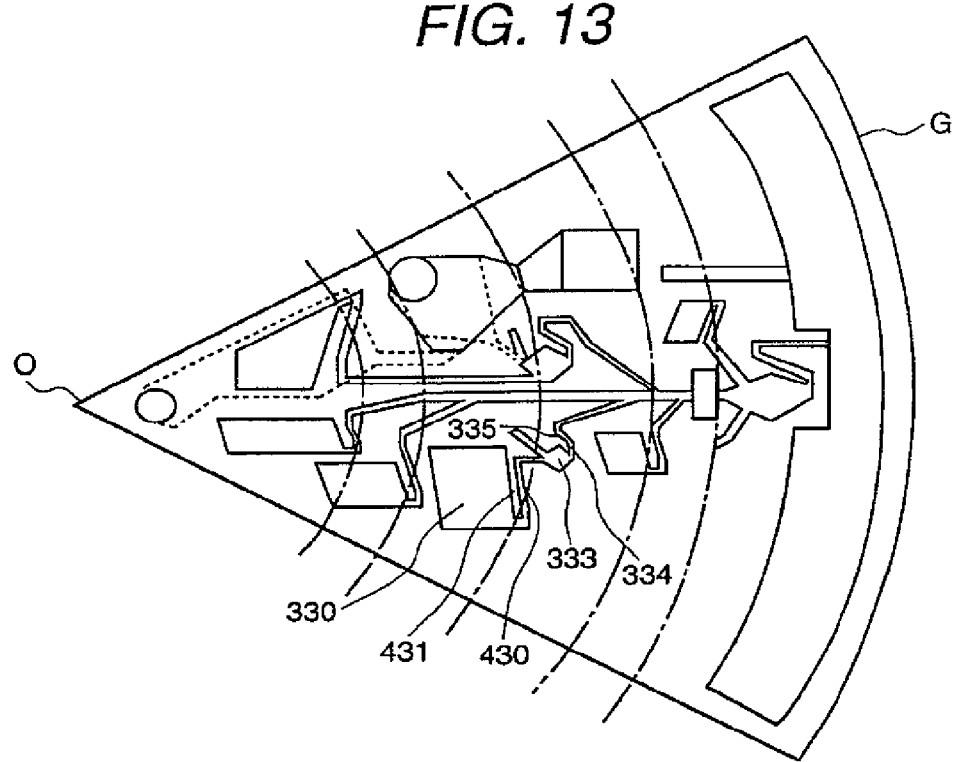
FIG. 13 is a top view of the analyzer according to an embodiment of the present invention.

In addition, as shown in FIG. 13, a first washing solution temporary holding container (washing solution temporary holding container) 333 is provided downstream of the flow path 430 which has the first washing solution return portion 431. If a second washing solution is provided at the downstream side to the flow path 334 which has the first washing solution holding container return portion 335 for returning the washing solution to the inner periphery side, even if the liquid remaining at the upstream side of the first temporary washing solution holding container 333 flows out, the liquid is held in the first temporary washing solution holding container, and thus it does not flow to the eluent recovery container side.

According to this invention, even if liquid remains in the reagent storing container or in the flow path, the liquid is held in the in the flow path and does not flow to the washing solution recovery container side. Thus, contamination caused by reagent from the previous step is prevented, and specific components of the liquid specimen such as nucleic acid can be extracted with high purity, and thus highly accurate analysis can be done.

Figure 14:
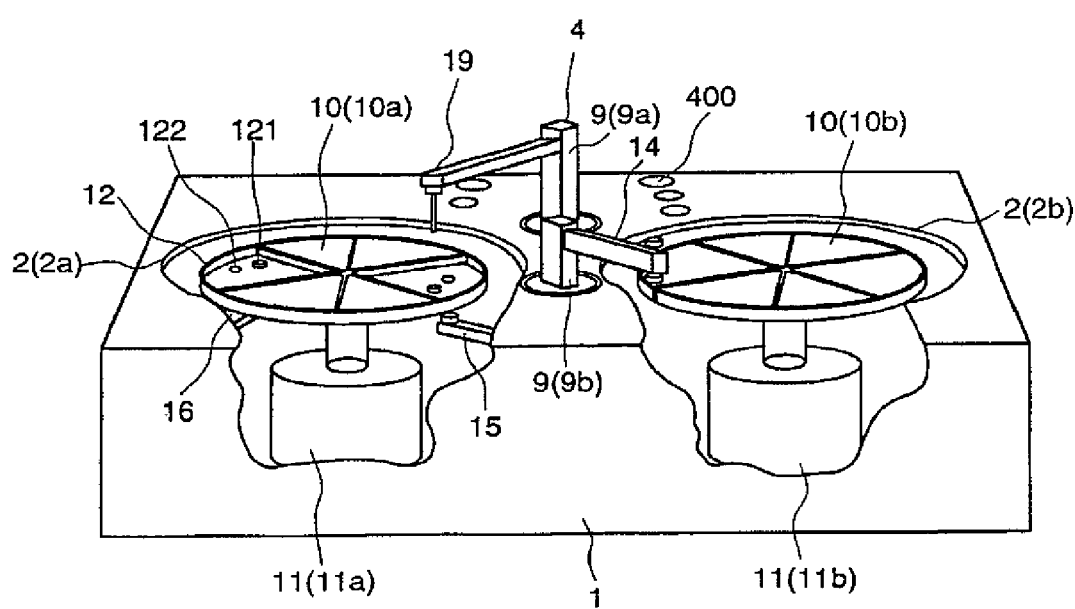
FIG. 14 is an overall structural view of the gene analyzer according to an embodiment of the present invention.

In the above invention, reagent flow is controlled by forming vent holes using a hole forming device, but a dispensation mechanism may also be used. That is to say, as shown in FIG. 14, a reagent dispenser is included, and after a prescribed amount of reagent is dispensed from each of the reagent bottles 400 using the reagent dispenser 19, into the reagent storage container shown in FIG. 3, the analysis disk is rotated and the reagent is caused to flow. The flow is shown in FIG. 15.

Figure 15:
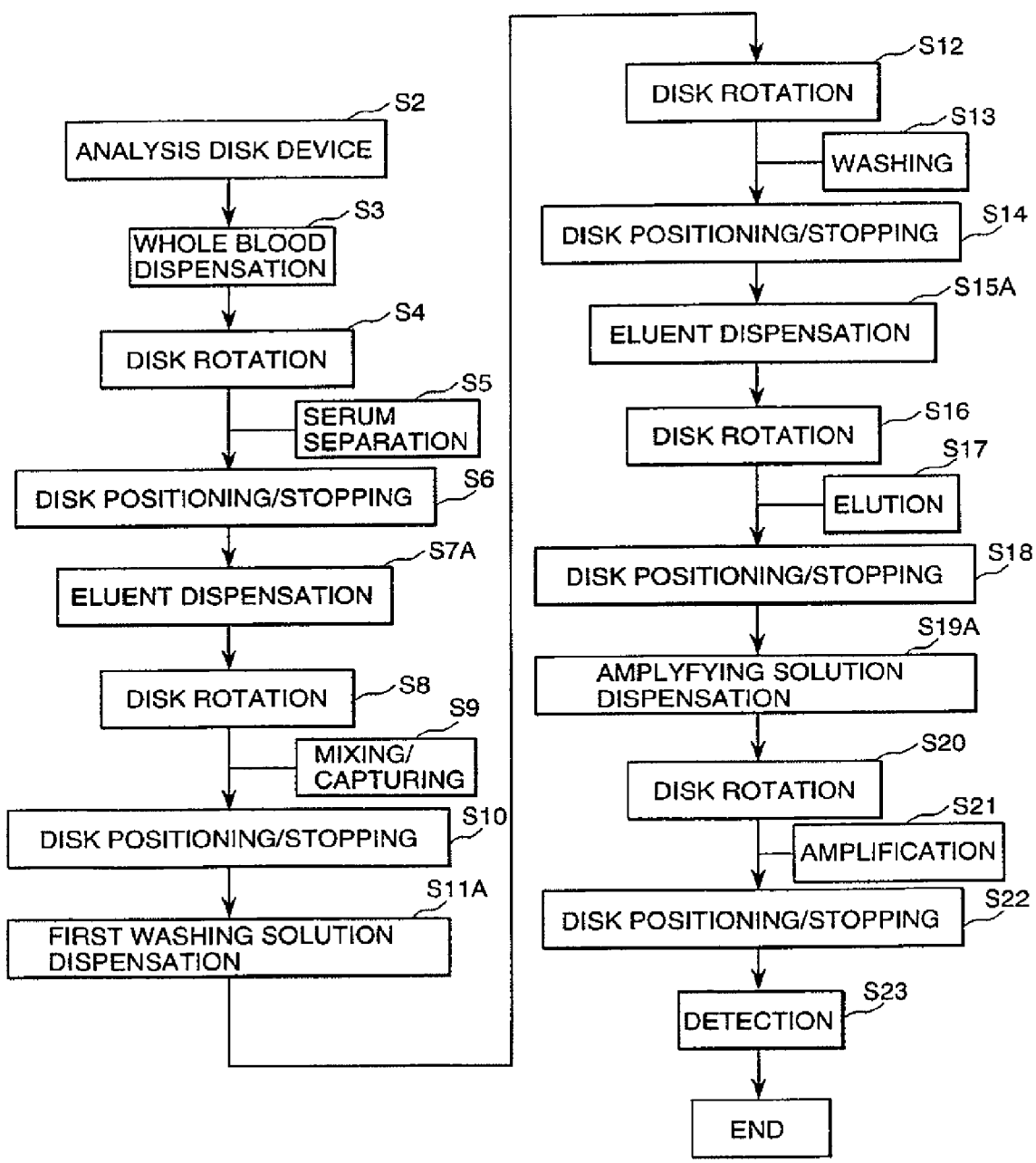
FIG. 15 is explanatory diagram showing the steps of the analysis operation according to an embodiment of the present invention.

In FIG. 15, the steps are essentially the same as those in FIG. 9(a), and the same steps are assigned the same numbers and detailed descriptions thereof are not repeated. "A" will be suffixed to the number for those steps that are similar. In FIG. 14, the flow starts from the analysis disk device (S2). Solution dispensation (S7A) is employed in place of solution vent hole formation (S7), and the reagent is dispensed by the reagent dispenser 9. The first washing solution vent hole formation (S11) is replaced by the first washing solution dispensation (S11A).

In addition, the eluent vent hole formation (S15) is replaced by the eluent dispensation (S15A).

According to this invention, there is no need to provide a valve for controlling the flow of the reagents in the middle of the flow path, and liquid does not remain on the valve portion in the flow path, and thus prevention of the contamination due to the reagent from the previous step is prevented, and specific components of the liquid specimen such as nucleic acid can be extracted with high purity, and thus high purity analysis can be done.

As described above, the chemical analyzer may be formed so as to be portable, and thus may be brought close to the hospital bed. That is to say, the chemical analyzer can be brought close to the patient or subject, and the whole blood test can be done while the medical examination is being done. As shown in step S2, after reagent is introduced into the necessary number of analyzers in accordance with the number of analyses being done, the analyzers are mounted onto the holding disk 12. In addition, the specimen is loaded into the specimen container 310. In this case, the examination is done immediately using 1 or 2 analyzers, and it is preferable that when these analyzers are loaded on the structure, a dummy analyzer is mounted (balance weight mounting) at the opposite surface in order to improve accuracy of the examination. The reagent is loaded into the analyzer in advance and sealed. The reagent or other liquid is loaded into the dummy analyzer as the dummy and then sealed. As a result, the phenomenon of agitation due to rotation is small.

Thus, at least 2 analyzers each of which comprises an outer frame container and a lid for covering this outer frame container, and in which storage containers for storing the chemical components separated from the specimen are provided on one side and arranged from the center portion inside the outer frame container; and some reagent containers excluding the storage containers are lined up on the other side, and the remaining containers are lined up on either the one side or on the other side; and an analysis section is disposed on the outer periphery side of each of these containers, and the inlet portion of each container is provided at the center side and the outlet portion is provided at the outside; and a discharge fluid storage container is provided outside the analysis section; and in which there are flow paths that connect the storage containers, the washing solution containers, and the analysis sections; and a chemical analysis method is provided in which, in one analyzer, the reagent container is loaded with reagent and then sealed and in the other analyzer, the reagent container is loaded with dummy fluid and then sealed; and the analyzers are loaded in a structure which is driven by a motor and is portable; and a specimen is loaded in the specimen container and is sealed; and chemical analysis is carried out when the structure rotates.

According to the present invention, it is not necessary to provide a valve for controlling the flow of each reagent in the middle of the flow path, and thus liquid does not remain on the valve portion that is in the middle of the flow path, and contamination due to the reagent from the previous step is prevented, and specific components of the liquid specimen such as nucleic acid can be extracted with high purity, and thus highly accurate analysis can be done.

What is claimed is:

1. An extractor comprising a structure body having an extracting device and a hole forming device, said structure body is supported so as to be rotatable, and said extracting device comprising a capturing section for capturing specific chemical components from a specimen and a plurality of reagent containers which hold liquid which will flow through said capturing section, wherein:

said plurality of reagent containers which are connected to said capturing section comprise a liquid outlet port which is provided at a side opposite to a rotation center, namely an outer periphery side, during rotation of said structure body;

said capturing section is held in said extracting device, closer to an outer periphery side than said plurality of reagent containers; and said reagent container comprises said liquid outlet port which is provided on said opposite side to said rotation center and a bent flow path portion which returns to said rotation center from said liquid outlet port, a most inner periphery portion of said bent flow path portion positioned at an outer periphery side from a most inner periphery portion of said reagent container, said reagent container is sealed with a cover which is enabled to form a hole, at a state before the hole in said cover is made, said reagent container communicates to an outside portion of said reagent container only at said liquid outlet port, and which at a particular stage prevents a flow of liquid from said reagent containers which are connected to said capturing sections, and at another stage, forms said liquid flow due to a centrifugal force from a rotation of said extracting device, and a vent hole is formed to a cover for sealing said reagent containers using said hole forming device.

2. A chemical analyzer comprising a structure body having an analyzing device and a hole forming device, said structure body is supported so as to be rotatable, said analyzing device comprising a capturing section for capturing specific chemical components from a specimen and specimen containers, and reagent containers, wherein:

said reagent container comprises a liquid outlet port which is provided at a periphery side opposite to a rotation center during rotation of said structure body;

said capturing section said reagent containers comprises a bent flow path portion which returns to said rotation center from said liquid outlet port, a most inner periphery portion of said bent flow path portion positions at an outer periphery side from a most inner periphery portion of said reagent container, said reagent container is sealed with a cover which is enabled to form a hole, at a state before the hole in said cover is made, said reagent container communicates to an outside portion of said reagent container only at said liquid outlet port is held in said analyzing device, closer to an outer periphery side than said specimen containers;

a flow path is provided which connects said capturing section with said reagent containers;

at said periphery side of said capturing section, in an amplifying solution storage container for introducing amplifying solution for amplification and detection, analysis sections are provided which are connected by a flow path which having a bent flow path portion which returns to a rotation center side than a position of a flow path outlet of said amplifying solution storage container, said most inner periphery portion of said bent flow path portion positions toward an outer periphery side than a most inner portion of said amplifying solution storage container, said amplifying solution storage container is sealed with a cover which is enabled to form a hole, at a state before the hole in said cover is made, said amplifying solution storage container communicates to an outside portion of said amplifying solution storage container only at said liquid outlet port, and a flow path outlet port from said amplifying solution storage container to said analysis section is provided at said outer periphery side.

3. A chemical analyzer according to claim 2, a discharge fluid storage container is arranged along a periphery and connected to said analysis section.

4. A chemical analyzer comprising a structure body having an analyzing device and a hole forming device, that is supported so as to be rotatable, said analyzing device comprising a capturing section for capturing specific nucleic acids from a specimen, specimen containers, serum storage containers, mixture containers in which reagents said specimen are mixed, and reagent containers which include washing solution containers, wherein:

said specimen container, said mixture container, and said washing solution container comprise a liquid outlet port which is provided at an outer periphery side opposite to a rotation center during rotation of said structure body, said nucleic acid capturing section is held in said analyzing device said washing solution containers comprises a bent flow path portion which returns to said rotation center from said liquid outlet port, a most inner periphery portion of said bent flow path portion positions at an outer periphery side from a most inner periphery portion of said washing solution container, said washing solution container is sealed with a cover which is enabled to form a hole, at a state before the hole in said cover is made, said washing solution container communicates to an outside portion of said washing solution container only at said liquid outlet port closer to said outer periphery side than said specimen containers, said reagent containers, and said washing solution containers;

a flow path is provided which connects said nucleic acid capturing section with said washing solution containers and the other reagent containers; and at said periphery side of said capturing section, to an amplifying solution storage container for introducing amplifying solution for amplification and detection, analysis sections are provided, which are connected by a flow path having a bent flow path portion which returns to a rotation center side than a position of a flow outlet of said amplifying solution storage container, said most inner periphery portion of said bent flow path portion positions toward an outer periphery side than a most inner portion of said amplifying solution storage container, said amplifying solution storage container is sealed with a cover which is enabled to form a hole, at a state before the hole in said cover is made, said amplifying solution storage container communicates to an outside portion of said amplifying solution storage container only at said liquid outlet port a flow path outlet port from said amplifying solution storage container to said analysis section is provided at said outer periphery side.

5. A chemical analyzer according to claim 4, discharge fluid storage containers are arranged along to a periphery and are connected to said analysis section.

6. A chemical analyzer according to claim 4, wherein the bent flow path portion of said flow path is closer to a rotation center than an outlet port of said mixture container and said washing solution container respectively.

7. An extractor according to claim 1, wherein:
said extractor has an optical device in which light is irradiated in said reagent container to heat said reagent.

* * * * *